United States Patent [19]
Jordan, Jr.

[11] 3,935,226
[45] Jan. 27, 1976

[54] SUBSTITUTED PHENANTHROLINE PIGMENTS

[75] Inventor: James J. Jordan, Jr., Livingston, N.J.

[73] Assignee: Allied Chemical Corporation, New York, N.Y.

[22] Filed: Sept. 23, 1974

[21] Appl. No.: 508,302

[52] U.S. Cl................................ 260/282; 260/272
[51] Int. Cl.².................................... C07D 487/06
[58] Field of Search............................ 260/282, 272

[56] References Cited
UNITED STATES PATENTS

| | | | |
|---|---|---|---|
| 1,935,945 | 11/1933 | Eckert | 260/282 |
| 2,965,644 | 12/1960 | Eckert | 260/282 |
| 3,632,589 | 1/1972 | Mueller | 260/282 |

FOREIGN PATENTS OR APPLICATIONS 2,246,110   4/1974   Germany
2,246,111   4/1974   Germany Primary Examiner—Richard J. Gallagher
Assistant Examiner—Mark L. Berch
Attorney, Agent, or Firm—Anthony J. Stewart; Jay P. Friedenson

[57]          ABSTRACT

Substituted phenanthroline pigments having the formula

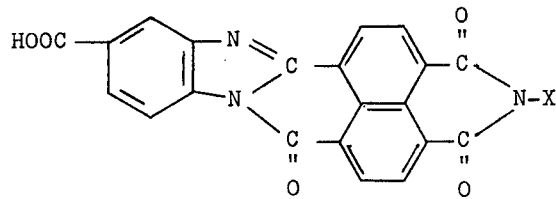

wherein X is hydrogen or methyl.

1 Claim, No Drawings

SUBSTITUTED PHENANTHROLINE PIGMENTS

This invention relates to novel pigment compositions. More particularly this invention relates to pigments comprising novel substituted phenanthroline compounds.

Pigments which are employed in automotive finishes desirably possess certain properties that render them particularly useful for this purpose. Ordinarily, they should be relatively, if not entirely, insoluble in organic solvents, heat-stable, give a strong shade and exhibit fastness to light. While there are numerous pigments in use today for automotive finishes, many of which possess all of these characteristics, much effort is constantly being expended to develop new pigments which qualify for this use. Lightfastness being probably the most important single characteristic in automotive finishes, it is this feature that is the most sought after as new pigment compositions are developed.

BRIEF DESCRIPTION OF THE INVENTION

Briefly, in accordance with this invention there is provided novel compounds, useful as pigments, having the formula:

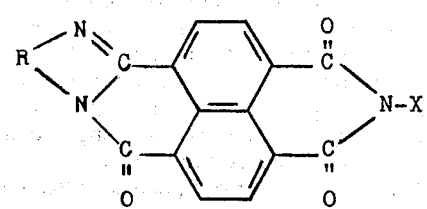

wherein X is hydrogen or methyl and R is phenylene, naphthylene or anthraquinonylene substituted with one to three substituents selected from chloro, bromo, carboxy, nitro, methyl, ethyl, methoxy, ethoxy or hydroxy. These compounds give a strong bright yellow to red shade, are insoluble in organic solvents, stable to heat and exhibit excellent light fastness. Particularly preferred are those compounds wherein X is hydrogen and R is disubstituted phenylene, i.e., 9,10-substituted benzimidazo [2,1-b]-2-hydrobenzo [1mn]-3,8-phenantholine-1,3,6-trione.

DETAILED DESCRIPTION OF THE INVENTION

The compounds of this invention may be prepared by condensing acenaphthene with dimethyl carbamoyl chloride followed by hydrolysis according to the reaction

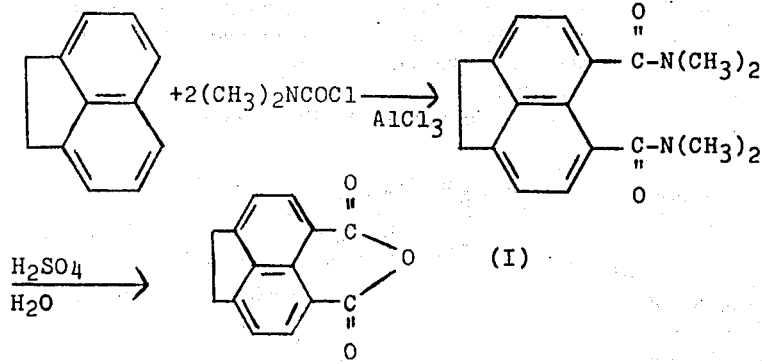

Reaction of (I) with ammonium hydroxide or methylamine results in

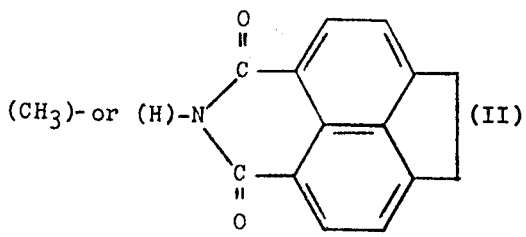

and oxidation of II with sodium dichromate yields

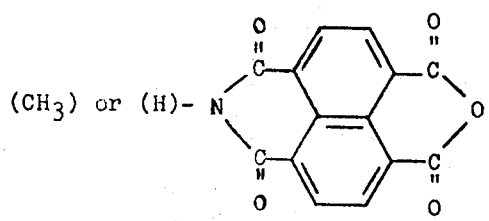

Thereafter, a substituted diamine which may be either a substituted phenylene diamine, a substituted naphthylene diamine or a substituted anthraquinonylene diamine is reacted with III by heating the two components, preferably above 80°C in an inert solvent such as glacial acetic acid or pyridine, to give

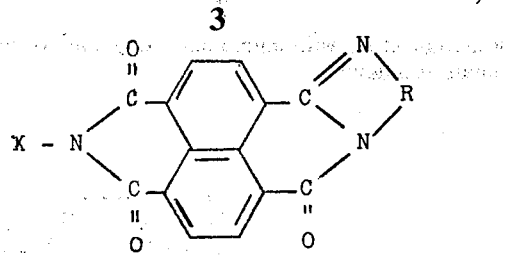

wherein X and R are as previously defined.

Exemplary of substituted diamines which may be reacted with (III) are:

4-nitro-o-phenylenediamine
4-methyl-o-phenylenediamine
4-carboxy-o-phenylenediamine
4-chloro-o-phenylenediamine
4,5-dichloro-o-phenylenediamine
4-bromo-m-phenylenediamine
4,5-dimethyl-o-phenylenediamine
5-chloro-m-phenylenediamine
5-nitro-m-phenylenediamine
4-methoxy-o-phenylenediamine
4-ethyl-5-chloro-o-phenylenediamine
4-ethoxy-m-phenylenediamine
4-hydroxy-o-phenylenediamine
4-nitro-1,8-naphthalenediamine
4,5-dichloro-1,8-naphthalenediamine
4-methoxy-1,8-naphthalenediamine
4,5-dimethyl-1,8-naphthalenediamine
4-nitro-1,2-diaminoanthraquinone
4,5-dichloro-1,2-diaminoanthraquinone, and the like.

Compounds similar to those of the present invention have been reported by Arient, et al, Coll. Czech. Chem. Commum., 30(11), 3718–29 (1965). However, the compounds disclosed by Arient, et al are not suitable as pigments for automotive finishes. Unexpectedly the presence of substituents on the diamines employed to produce the compounds of this invention results in a pigment which has greatly superior lightfastness vis-a-vis the unsubstituted compounds of Arient, et al. For example, 9-nitro benzimidazo [2, 1-b]-2-hydrobenzo [1mn]-3,8-phenanthroline-1,3,6-trione exhibits a lightfastness 50% greater than unsubstituted benzimidazo [2, 1-b]-2-hydrobenzo [1mn]-3,8-phenantholine-1,3,6-trione. The other substituents mentioned herein likewise produce pigments having superior lightfastness compared to the unsubstituted compounds.

DESCRIPTION OF THE PREFERRED EMBODIMENTS

The following examples are given by way of illustration only.

EXAMPLE I

A mixture of 1 mole of acenaphthene, 2.5 moles of dimethylcarbamoylchloride and 2.6 moles of anhydrous aluminum chloride in chlorobenzene is heated for 3 hours at 130°C. The product is refluxed for 20 minutes in 60 percent H$_2$SO$_4$ to yield acenaphthene-5,6-dicarboxylic anhydride. This product is refluxed with ammonium hydroxide for several hours, dried and oxidized with sodium dichromate in glacial acetic acid for 3 hours yielding a product identified as 2-hydrobenzo [de] isoquinoline-1,3-dione-6,7-dicarboxylic anhydride.

26.7 grams of the product obtained and 15.3 grams of 4-nitro-o-phenylenediamine in 500 grams of glacial acetic acid are brought to reflux within 15 minutes with stirring. A thick yellow precipitate forms quickly. Refluxing is continued for 3 hours and the precipitate is filtered, washed with glacial acetic acid and then water to yield 36 grams of a strongly colored yellow pigment exhibiting excellent lightfastness, temperature stability and resistance to solvents. The product is identified as 9-nitrobenzimidazo [2, 1-b]-2-hydrobenzo [1mn]-3,8-phenantholine-1,3,6-trione.

EXAMPLES II – VII 26.7 g. of 2-hydrobenzo [de] isoquinoline-1,3-dione-6,7-dicarboxylic anhydride are added to 500 g. of glacial acetic acid and the temperature is raised to 80°. While stirring well, 12.2 g. of 4-methyl-o-phenylenediamine are added and the whole is brought to reflux within 30 minutes. A thick orange precipitate quickly forms. It is refluxed for 3 hours, filtered hot, washed with glacial acetic acid then with water and dried to yield 34 g. of a strongly colored orange pigment which is distinguished by excellent fastness to light, temperature stability, and resistance to solvents.

If the 12.2 g. of 4-methyl-o-phenylenediamine are replaced by equimolar amounts of one of the following diamines given below, then with the same procedure, similar fast pigments are obtained.

| Example No. | Amine | Shade |
| --- | --- | --- |
| III. | 4-carboxy-o-phenylenediamine | orange |
| IV. | 4-chloro-o-phenylenediamine | orange |
| V. | 4,5-dichloro-o-phenylenediamine | orange |
| VI. | 4,5-dimethyl-o-phenylenediamine | red |
| VII. | 4-methoxy-o-phenylenediamine | red |

EXAMPLE VIII 28.1 g. of 2-methyl-2H-benzo [de] isoquinoline-1,3-dione-6,7-dicarboxylic anhydride and 15.3 g. of 4-nitro-o-phenylenediamine in 500 g. of glacial acetic acid are brought to reflux within 1 hour while stirring well. A thick yellow precipitate quickly forms. It is refluxed for 3 hours, filtered hot, washed with glacial acetic acid then with alcohol and dried to yield 38 g. of a strongly colored yellow pigment which is distinguished by excellent fastness to light, temperature stability, and resistance to solvents.

I claim:

1. A compound having the formula

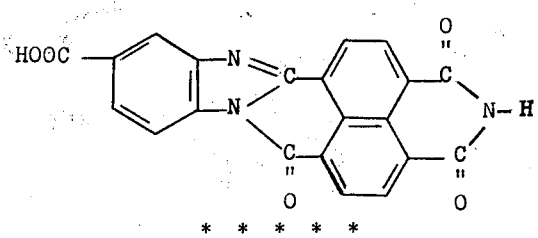

* * * * *